United States Patent [19]

Rosenblatt et al.

[11] Patent Number: 5,087,562
[45] Date of Patent: Feb. 11, 1992

[54] HUMORAL HYPERCALCEMIC FACTOR ANTAGONISTS WITH MODIFICATION AT POSITION 13 . . .

[75] Inventors: Michael Rosenblatt, Ardmore; Eliahu Roubini, Lensvale, both of Pa.; Michael Chorev, Jerusalem, Israel; Ruth F. Nutt, Green Lane, Pa.

[73] Assignee: Merck & Co., Inc., Rahway, N.J.

[21] Appl. No.: 514,633

[22] Filed: Apr. 25, 1990

[51] Int. Cl.$^5$ .............. G01N 33/567; C07K 7/10; A61K 37/24
[52] U.S. Cl. .................. 435/7.21; 435/7.5; 530/324; 530/325; 514/12; 436/501; 930/290; 930/DIG. 820
[58] Field of Search ............. 530/324, 325; 514/12; 436/501; 930/290, DIG. 820; 435/7.21, 7.5

[56] References Cited

PUBLICATIONS

Juppner et al., Biochemistry, vol. 29 (30), pp. 6941–6, ()1990)≈Chem. Abs. 113(15), 126872f.
Coltrera et al., American Chem. Society, vol. 19, No. 18, pp. 4380–4384, (1980).
The Merck Manual, 11th ed., (1966), pp. 452–53.

*Primary Examiner*—John Doll
*Assistant Examiner*—T. Wissendorf
*Attorney, Agent, or Firm*—Salvatore C. Mitri; Charles M. Caruso

[57] ABSTRACT

The present invention relates to the use of peptide analogues as inhibitors of their respective naturally occurring peptides. The structure of the peptide hormone analogues is exemplified by human humoral hypercalcemic factor (hHCF), wherein Lys$^{13}$ is modified so as to produce HCF analogues which can inhibit the action of HCF.

3 Claims, No Drawings

HUMORAL HYPERCALCEMIC FACTOR ANTAGONISTS WITH MODIFICATION AT POSITION 13 ...

FIELD OF THE INVENTION

This invention relates to the use of peptide analogues useful in inhibiting the naturally occurring peptide in vivo and in vitro. These peptide analogues when administered to a vertebrate, such as mammals, block the activity of the peptide or other analogous molecules.

BACKGROUND OF THE INVENTION

The peptide analogues of this invention are useful in treating various diseases caused by an excess of the naturally occurring peptide and in treating peptide dependent tumors. One example of this invention relates to the use and synthesis of humoral hypercalcemic factor (HCF) analogues useful for inhibiting the action of HCF both in vivo and in vitro.

Investigators have isolated and obtained partial amino acid sequences of peptide derived from several different human tumors (lung squamous carcinoma, renal cell carcinoma, and breast carcinoma). J. M. Moseley et al., Proc. Natl. Acad. Sci. U.S.A. 84, 5048 (1987); G. J. Strewler et al., J. Clin. Invest., 80, 1803 (1987); A. F. Stewart et al., Biochem. Biophys. Res. Commun. 146, 672 (1987); M. Mangin et. al., Proc. Natl. Acad. Sci. U.S.A., 85, 597 (1988). One group published the putative full-length peptide structure (141 amino acids) based on the complementary DNA (cDNA) nucleotide sequence. L. J. Suva et al., Science 237, 893 (1987).

Human "humoral hypercalcemic factor" (hHCF) is considered to be related in biological effects to parathyroid hormone (PTH). HCF shows considerable homology to the biologically critical $NH_2$-terminal region of PTH. However, there are significant differences in the peptide sequences between PTH and HCF, and this new factor appears to be the product of a different gene. L. J. Suva et al., Science 237, 893 (1987).

Previously, it had been proposed that tumors could secrete PTH ectopically and cause hypercalcemia of malignancy. Several studies demonstrated that a PTH-like factor, physicochemically and immunologically distinct from PTH, is secreted by tumor cells. S. B. Rodan et al. J. Clin. Invest. 72, 1511 (1983); A. F. Stewart et al., Proc. Natl. Acad. Sci. U.S.A., 80, 1454 (1983); G. J. Strewler et al., J. Clin. Invest. 71, 769 (1983). However, messenger RNA for PTH was not found in such tumors. It was also known that this PTH-like factor stimulates adenylate cyclase in PTH target cells, and that this activity can be inhibited by PTH antagonists. Thus, it is presently considered that HCF is a factor that is responsible for hypercalcemia of malignancy by its secretion from the tumor and its altering effect on calcium metabolism.

It is, therefore, an object of the present invention to provide antagonists of HCF. If a peptide analogue of HCF could be constructed which would bind with the cell surface receptor of HCF with same or greater affinity than the naturally occurring peptide, then the peptide analogue could be used to block the effect of the naturally occurring peptide. Thus, it is also an object of the present invention to provide peptide analogues useful for the treatment of hypercalcemia of malignancy.

Another object of the present invention is to provide novel HCF analogues. Other objects of the present invention are to provide methods of inhibiting the action of HCF through the administration of novel HCF analogues. Still another object of the invention is to provide HCF analogues wherein amino acid modifications result in binding to the cell surface receptors without activating a second messenger molecule. The above and other objects are accomplished by the present invention in the manner more fully described below.

SUMMARY OF THE INVENTION

The present invention provides peptides having the formula hHCF(7-34)$NH_2$, desamino[$Asn^{10}$, $Leu^{11}$, D-$Trp^{12}$]hHCF(7-34)$NH_2$, desamino[$Asn^{10}$, $Leu^{11}$]hHCF(7-34)$NH_2$, desamino[D-$Trp^{12}$]hHCF(7-34)$NH_2$, desamino[$Asn^{10}$, $Leu^{11}$, D-$Trp^{12}$]hHCF(8-34)$NH_2$, desamino[D-$Trp^{12}$]hHCF(8-34)$NH_2$, desamino[$Leu^{11}$, D-$Trp^{12}$]hHCF(7-34)$NH_2$, desamino[$Asn^{10}$, $Leu^{11}$]hHCF(8-34)$NH_2$, and desamino [$Leu^{11}$, D-$Trp^{12}$]hHCF(8-34)$NH_2$, wherein $Lys^{13}$ is modified in the epsilon-amino acid group by N,N-diisobutyl or 3-phenylpropanoyl. The above-mentioned peptides can be used in a method of acting upon a HCF receptor which comprises administering a therapeutically effective but non-toxic amount of such peptide to a mammal. Additionally, an in vitro bioassay of HCF, wherein a measured amount of such peptides inhibits binding of HCF to a HCF receptor in vitro is an aspect of the present invention. A pharmaceutical composition containing a pharmaceutically acceptable carrier and, dispersed therein, a therapeutically effective but non-toxic amount of such peptide is another feature of this invention.

DETAILED DESCRIPTION OF THE INVENTION

The HCF antagonist compounds of this invention are illustrated by peptides having the formula hHCF(7-34)$NH_2$, desamino[$Asn^{10}$, $Leu^{11}$, D-$Trp^{12}$]hHCF(7-34)$NH_2$, desamino[$Asn^{10}$, $Leu^{11}$]hHCF(7-34)$NH_2$, desamino[D-$Trp^{12}$]hHCF(7-34)$NH_2$, desamino[$Asn^{10}$, $Leu^{11}$, D-$Trp^{12}$]hHCF(8-34)$NH_2$, desamino[D-$Trp^{12}$]hHCF(8-34)$NH_2$, desamino[$Leu^{11}$, D-$Trp^{12}$]hHCF(7-34)$NH_2$, desamino[$Asn^{10}$, $Leu^{11}$]hHCF(8-34)$NH_2$, and desamino [$Leu^{11}$, D-$Trp^{12}$]hHCF(8-34)$NH_2$, wherein $Lys^{13}$ is modified in the epsilon-amino acid group by N,N-diisobutyl or 3-phenylpropanoyl.

One representative example of a peptide analogue of the present invention is desamino [$Leu^{11}$, D-$Trp^{12}$, $Lys^{13}$($N^\epsilon$—$CO(CH_2)_2$-Phenyl)]hHCF(8-34)$NH_2$. This representative example should not be construed as limiting the invention. Various other objects, features and advantages of the present invention will be more fully discussed from the following detailed description.

Extensive structure and activity studies have now led to the design of peptide analogues which have high binding affinity for their respective cell surface receptors while not stimulating the production of second messenger molecules. HCF analogues with two to six amino acids removed from the N-terminus produces an inhibitor which still binds with high affinity to the peptide hormone receptor without causing a change in cyclic AMP concentration.

The following is the 34-amino acid sequence of human humoral hypercalcemia factor (hHCF): Ala- Val-Ser-Glu-His(5)-Gln-Leu-Leu-His-Asp(10)-Lys-Gly-Lys-Ser-Ile(15)-Gln-Asp-Leu-Arg-Arg-(20)-Arg-Phe-Phe-Leu-His(25)-His-Leu-Ile-Ala-Glu-(30)-Ile-His-Thr-Ala. The peptide art designations contained herein are as follows: Ala, Alanine; Val, Valine; Ser, Serine; Phe, Phenylalanine; His, Histidine; Gln, Glutamine; Leu, Leucine; Asp, Aspartic acid; Lys, Lysine; Gly, Glycine; Ile, Isoleucine; Arg, Arginine; Glu, Glutamic acid; Asn, Asparagine, and Thr, Threonine. These standard abbreviations are well recognized in the art of peptide chemistry. It is also well recognized that 3-phenylpropanoyl is represented by the chemical formula ($N^\epsilon$—$CO(CH_2)_2$-Phenyl).

The present invention further provides a method of inhibiting the action of HCF comprising the administration of therapeutically effective but non-toxic amount of HCF analogues described above. The present invention also provides a method of treating osteoporosis or hypercalcemia comprising the administration of a therapeutically effective but non-toxic amount of HCF analogues described above. A method of treating hyperparathyroidism comprising the administration of a therapeutically effective but non-toxic amount of the HCF analogues of this invention is also provided. A method of treating hyperparathyroidism expressed as a hypercalcemic crisis, renal failure or hypertension is also provided. A method of treating the disease state produced by a tumor or other cell overproducing a peptide hormone-like molecule and method of treating immune diseases wherein the disease state is manifested by inflammation, an allergic response, or hyperactive lymphocytes is also provided by the novel peptide analogues of the present invention.

Fragments of peptide, containing the region specific for binding to the cell surface receptor, can be used as inhibitors or blocking agents. For HCF, it is considered that the N-terminal 34 amino acids are sufficient to define binding specificity to the cell surface receptor.

The presence of D-amino acids in a peptide in place of L-amino acids results in a peptide resistant to catabolism. Substitutions which result in active peptide are considered to be within the scope of the present invention. The utilization of D-amino acids in peptide hormone synthesis is described in the following publications herein incorporated by reference: Coltrera, et al., Biochemistry, 19: 4380–4385, 1980; Rosenblatt et al., Biochemistry, 20: 7246–7250, 1981. Additionally, substitutions of amino acids which are equivalent to the amino acids disclosed herein is considered to be within the scope of the present invention.

The balance of the description will be divided into two sections. Section I will describe the preparation and structure of peptide hormone inhibitors. Section II will discuss the use of the peptide hormone inhibitors.

I. PREPARATION AND STRUCTURE OF PEPTIDE HORMONE INHIBITORS

The technique of solid-phase peptide synthesis, developed by Merrifield "Solid-Phase Peptide Synthesis", Advances in Enzymology, 32: 221–296, (1969); G. Barany and R. B. Merrifield "Solid-Phase Peptide Synthesis", The Peptides, volume 2, editors: E. Gross & J. Meienhofer (1980) has been successfully employed in the synthesis of peptides including HCF. This method is based on the strategy of having the carboxyl terminus of the peptide linked covalently to a solid support. The desired peptide sequence is prepared by stepwise coupling of single amino acids to a peptide chain growing from the carboxyl toward the amino terminus. Coupling is typically achieved by activation of the carboxyl group of the amino acid being attached to the resin, which may have other potentially reactive groups blocked. Following addition of an amino acid to the growing polypeptide chain, and prior to further chain elongation, a protecting group is typically removed. Because each amino acid is coupled by nearly the same series of reactions, the need for elaborate strategies in the synthesis is minimized. Solubility is not a major issue during synthesis, because the peptide is linked to a solid support. This method is rapid and it can be utilized by a single worker. It is very convenient for the synthesis of multiple analogues with amino-terminal substitutions, because a single synthesis can be branched in multiple directions near the amino terminus, thereby creating many analogues varying only in the amino terminal region. In addition, modification of the $\epsilon$-amino group of lysine can be achieved by the use of a unique protecting group (Fmoc) which can be selectively removed and then modified by a standard coupling cycle, omitting removal of the N-terminal Boc group.

II. USE OF PEPTIDE HORMONE INHIBITORS

The method of inhibiting the action of HCF peptide comprises the administration of a therapeutically effective but non-toxic amount of any HCF peptide analogue. These peptide analogues retain specificity for the cell surface receptor without stimulating a physiological response. This method of use applies to the entire peptide or its analogue, or to a fragment of the peptide or analogue containing the receptor binding site.

The use of peptide analogues is exemplified by HCF analogues. The HCF is of human origin, but HCF of bovine, rat or any mammalian source origin may prove to be equivalent to the human HCF. The analogue may contain all the amino acids indicated, or additionally, truncations or elongations. Individual amino acids can be substituted to improve biological or chemical stability.

The peptide analogues of this invention can be used in vitro to measure the concentration of naturally occurring peptide. This bioassay procedure is illustrated by a bioassay for HCF. The unknown concentration of HCF in a solution can be determined by measuring the amount of HCF analogue required to inhibit its binding to the HCF cell surface receptor. The concentration of HCF analogue required to block the action of HCF is a direct indicator of the HCF concentration.

HCF analogues can be used to diagnose the etiology of or to treat osteoporosis or hypercalcemia through the administration of a therapeutically effective but non-toxic amount of the HCF analogues of this invention. Similarly, hyperparathyroidism and other aspects of hyperparathyroidism, such as a hypercalcemic crisis, renal failure or hypertension can be treated through the administration of the HCF analogues of this invention.

Tumors and other aberrant cell growth often produce hormone-like substances causing a disease state. The use of peptide analogues to block stimulation caused by such hormone-like substances can result in the alleviation of the disease state. An example of this is the humoral hypercalcemic factor of malignancy. Therefore, the HCF peptide analogues of the present invention can be administered to treat diseases caused by aberrant production of hormone like substances.

The peptide analogues of this invention exhibit both oral and parenteral activity and can be formulated in dosage forms for oral, parenteral, intra-nasal, or topical administration in a non-toxic but effective amount, preferably dispersed in a pharmaceutically acceptable carrier. The dosage units of active ingredient in the pharmaceutical compositions of this invention may be varied; however, it is necessary that the amount of the active ingredient shall be such that a suitable dosage form is obtained. The selected dosage form depends upon the desired therapeutic effect, on the route of administration, and on the duration of treatment.

Solid dosage forms for oral administration include capsules, tablets, pills, powders and granules. In such solid dosage forms, the active compound is admixed with at least one inert diluent such as sucrose, lactose or starch. Such dosage forms can also contain, as is normal practice, additional substances other than inert diluent. In the case of capsules, tablets, and pills, the dosage forms may also contain buffering agents. Tablets and pills can additionally be prepared with an enteric coating.

Liquid dosage forms for oral administration include pharmaceutically acceptable emulsions, solutions, suspensions, syrups and elixers containing inert diluents commonly used in the pharmaceutical art. Besides inert diluents, such compositions can also include adjuvants, such as wetting agents, emulsifying and suspending agents, and sweetening agents. Preparations according to this invention for parenteral administration include sterile aqueous or non-aqueous solutions, suspensions or emulsions. Examples of such solutions, suspensions or emulsions are propylene glycol, polyethylene glycol, vegetable oils such as olive oil and injectable organic esters such as ethyloleate.

EXAMPLES

Examples provided are intended to assist in a further understanding of the invention. Particular materials employed, species and conditions are intended to be further illustrative of the invention and not limitative of the reasonable scope thereof.

EXAMPLE 1

Synthesis and Purification of Peptide Analogues of HCF

Analogues of HCF were prepared by a modification of the solid-phase method of Merrifield. Syntheses were performed using an Applied Biosystems 430A Automated Peptide Synthesizer. 4-Methyl-benzhydrylamine hydrochloride resin (polystyrene-1% by divinylbenzene, USB) was employed as the solid support in order to effect the carboxyamide (CONH2) COOH-terminal modification.

The tertiary butyloxycarbonyl (Boc) group was used to protect the alpha-amino group of each amino acid during coupling. Side-function protection was afforded as follows: (a) the hydroxyl group of serine and threonine were protected as the O-benzyl ether (Bzl); (b) the hydroxyl group of tryosine as the 0-2,6-dichlorobenzyl ether (DCB) or p-bromobenzyloxycarbonyl ester (Brz); (c) the carboxyl group of glutamic and aspartic acid as the benzyl (Bz) or cyclohexyl ester (Chx); and (d) the imidazole nitrogen of histidine by the benzyloxymethyl (BOM) and the guanidine function of arginine was protected by the p-toluene-sulfonyl (Tos) group, and the indole imine by formyl groups (For); and (e) the lysine epsilon amino group by 2-chlorobenzyloxycarbonyl (ClZ) or Fluorenyl methyloxy carbonyl (Fmoc). All amino acids were obtained from Applied Biosystems, Inc., Peninsula Laboratories, or Bachem Chemicals.

The peptide-resin syntheses were carried out using Applied Biosystems, Inc. specified protocols. Double couplings were carried out for the incorporation of each amino acid. After the final coupling of each of the arginines (residues 18-21) the remaining free amino acid groups were acetylated to prevent generation of deletion peptides. Deprotection times with trifluoroacetic acid (TFA) were extended 6 minutes over manufacturer protocols. The substitution of the $\epsilon$-NH2 of Lys$^{13}$ required the following modifications in the synthetic procedure described previously: 1. incorporation of the N$\alpha$-Boc-Lys($\epsilon$-Fmoc)-OH in position 13; and 2. $\epsilon$-amino Fmoc deprotection and modification of the free $\epsilon$-NH2 in Lys$^{13}$.

Coupling of Boc-Lys($\epsilon$-Fmoc)-OH (0.94 g, 2.0 mmol) to the free amino terminus of [side chain protected Nle$^{10}$,Tyr$^{34}$]bPTH(14-34)pMBHA-® (0.25 mmol) was carried out in the standard manner (1 mmol of preformed symmetrical anhydride). The recoupling of Boc-Lys($\epsilon$-Fmoc)-OH was performed in the presence of 5% diisopropylethylamine (DIPEA) in DMF and followed with consecutive washes; $CH_2Cl_2$ (1×1 min) and DMF (1×1 min)

Removal of $\epsilon$-Fmoc protecting group was carried out in the standard manner. The protected resin-bound peptide was treated with 20% piperidine in DMF (1×1 min followed by 1×20 min). The resin was consecutively washed with MeOH (1×1 min), $CH_2Cl_2$ (4×1 min) and DMF (2×1 min). Acylation of $\epsilon$-amino in Lys$^{13}$ with 3-Phenypropanoyl was carried out in the standard manner. Two consecutive couplings of DCC preformed 3-phenylpropionic anhydride (2 mmol each) to the $\epsilon$-amino free side-chain protected resin-bound [Nle$^{18}$, Tyr$^{34}$]bPTH(13-34) were carried out and followed by a sequence of washes; $CH_2Cl_2$ (1×1 min), DMF (1×1 min), MeOH (1×1 min), $CH_2Cl_2$ (1×1 min) and MeOH (1×1 min). Testing with ninhydrin indicated the completion of the reaction, which was then followed by further washings; $CH_2Cl_2$ (4×1 min) and DMF (2×1 min).

Reductive alkylation of $\epsilon$-amino in Lys$^{13}$ with isobutyraldehyde was carried out in the standard manner. The free $\epsilon$-amino free side-chain protected resin-bound [Nle$^{18}$, Tyr$^{34}$]bPTH(13-34) was treated with isobutyraldehyde (0.072 mL, 1.25 mmol) in 1% AcOH/DMF (10 mL) followed by portionwise addition of NaCNBH$_3$ (79 mg, 1.25 mmol) over 40 min. After 1 hour the reaction mixture was filtered off and repeated with 20-fold excess of reagent which were allowed to react overnight. The resin was then washed in the following sequence; $CH_2Cl_2$ (3×1 min), DMF (2×1 min), MeOH (1×1 min) (negative ninhydrin test), $CH_2Cl_2$ (4×1 min), ethanol (2×1 min), and DMF (2×1 min).

The peptide was cleaved from the copolymer resin with simultaneous removal of the side-chain protecting groups similar to the 2 step HF cleavage procedure described by Tam, J.A.C.S. 105: 6442-6455 (1983). In the first HF step, the following ratios of reagents were used: 5% p-cresol, 5% p-thiocresol, 65% dimethyl sulfide and 25% HF. 10 ml of mixture per gram of peptide-resin was used for 2 hours at 0° C. In the second HF step the following ratio of reagents were used: 5% p-cresol, 5% p-thiocresol and 90% HF. The cleavage was carried out for 75 min. at 0° C. After removal of HF the peptide-resin mixture was washed with anhydrous ether to remove scavenger. The peptide was then extracted with 50% acetic acid and water. The washes were combined and chromatographed using Sephadex G-50F, eluting with 50% HOAc.

After lyophilization, the partially purified peptide was chromatographed by reverse phase HPLC (Vydac $C_4$ bonded silica, 15μ particle size, 300A pore size, using an aqueous acetonitrile gradient 10–50% B for 200 min (A=5% ACN/95% $H_2O$, 0.1% TFA, B=100% Acetonitrile 0.1% TFA) at a flow rate of 100 ml/min and monitored at 214 nm). Fractions through the peak were analyzed by analytical reversed phase HPLC and the fractions containing a single peak were pooled and lyophilized.

EXAMPLE 2
HCF Binding Assay Results

HCF analogues were analysed in a new receptor assay which modified the assay reported in Rosenblatt et al., Endocrin 107: 545–550 (1980). The binding assay used [$Nle^{8,18}$, ($^{125}I$)-$Tyr^{34}$]bPTH (1-34)$NH_2$ which was purified by HPLC (Novapak $C_{18}$, 32–35% $CH_3CN$ in 0.1% TFA) and was stored as aliquots in 25 mM TrisHCl/1%BSA at −70° C. Bovine renal cortical plasma membranes were incubated with radioligand (25,000 cpm) in a Tris-containing buffer (250 μl) for 30 min. at 21° C. Once equilibrium was reached, bound and free radioligand were separated by centrifugation.

High specific binding (85%) to bovine renal cortical membranes was obtained consistently.

| Structure | Binding $K_B$ (nM) |
|---|---|
| desamino[$Leu^{11}$,D-$Trp^{12}$,$Lys^{13}$ ($N^\epsilon$—$CO(CH_2)_2$-Phenyl)] hHCF(8-34)$NH_2$ | 20 ± 3 |

The assay reported on page 546 in Rosenblatt, et al. is as follows:

Radioligand binding assay: A PTH-binding assay based on the sulfur-free $^{125}I$-labeled hormone analog, [Nle-8,Nle-18,Tyr-34]-bPTH-(1-34)amide, was employed (4). The assay is specific and saturable with regard to PTH binding, and binding avidity in this system correlates closely with biological acitibity for multiple PTH agonist fragments and analogs. The specific activity for multiple PTH agonist fragments and analogs. The specific activity of the $^{125}I$-labeled ligand was 500±75 mCi/mg. Canine renal cortical membranes were purified by ultracentrifugation using discontinous gradients of sucrose in a manner identical to that used in previous studies of inhibitory potency (6, 10). Inhibition of specific binding of radioligand was assessed for each fragment over several log orders of magnitude. The concentration range employed was $1 \times 10^{-10}$ to $1 \times 10^{-2}$M. A total of 12 separate assays was performed in order to test each of the 7 peptides at least 3 times. In each assay, inhibition of radioligand binding was determined in triplicate at each concentration of peptide used.

EXAMPLE 3
Bovine Renal Membrane Adenylate Cyclase

HCF analogues were analyzed in a bovine renal membrane adenylate cyclase assay as described in Horiuchi et al., Science 238, 1566 (1987); Goldman et al., Endocin (in press). 3 nM [$Nle^{8,18}$,$Tyr^{34}$]bPTH(1-34)$NH_2$ or 30 nM HCF(1-34) $NH_2$ were used to stimulate adenylate cyclase.

| Structure | Adenylate Cyclase $K_I$ (nM) |
|---|---|
| desamino[$Leu^{11}$,D-$Trp^{12}$,$Lys^{13}$ ($N^\epsilon$—$CO(CH_2)_2$-Phenyl)] hHCF(8-34)$NH_2$ | 42 ± 5 |

As described by Goldman, et al on page 1470, the adenylate cyclase assay was obtained as follows:

Adenylate cyclase assay: Triplicate samples were incubated in a final volume of 250 μl consisting of buffer (40 mM Tris-HCl, 2 mM $MgCl_2$, 0.2 mM EGTA, 0.28 mM mangnesium ATP, 0.01 mM GTP, 2 mM isobutylmethylxanthine, 26.3 mM phosphocreatine, 22 U/ml creatine phosphokinase, and 0.1% BSA, pH 7.5), renal cortical membranes (55 μg protein/tube), and test compounds. Incubations were carried out for 30 minutes at 30° C. The tubes were then placed in a boiling water bath for 3 minutes and refrigerated. After centrifugation, cAMP formation was quantified using a competitive protein binding assay (22). Analogs devoid of adenylate cyclase-enhancing activity were tested for antagonist activity by measuring the inhibition of 3 nM [$Nle^{8,18}$,$Tyr^{34}$]bPTH-(1-34)$NH_2$-stimulated adenylate cyclase activity by each compound.

With regard to this assay, Horiuchi et al., disclose on page 1567 that:

In an adenylate cyclase assay in which we used bovine renal cortical membranes (17), hHCF-(1-34)$NH_2$ had a potency comparable to PTH. A close correspondence between renal binding ($K_b$) and activation constants (adenylate cyclase stimulation, $K_m$) was observed for all peptides tested (Table 1), although formal statistical comparison was not performed.

EXAMPLE 4
B10 Adenylate Cyclase Assay Results

HCF analogues were analyzed in a human osteosarcoma cell line, B10, for the ability to inhibit cAMP stimulation by 1 nM [$Nle^{8,18}$,$Tyr^{34}$] bPTH(1-34) $NH_2$ by the method described by R. J. Majeska et al, Endocrinol. 107, 1494 (1980).

| Structure | Adenylate Cyclase $K_I$ (nM) |
|---|---|
| desamino[$Leu^{11}$,D-$Trp^{12}$,$Lys^{13}$ ($N^\epsilon$—$CO(CH_2)_2$-Phenyl)] hHCF(8-34)$NH_2$ | 7.03 |

With regard to Example 4 above, Majeska, et al., on page 1495 describe the andenylate cyclase assay as follows:

Adenylate cyclase assay: Confluent cultures were rinsed in CMFH and scraped into 0.5–1.0 ml buffer (10 mM Tris-HCl, pH 7.8; 1 mM dithiothreitol, 0.2 mM $MgCl_2$; and 0.5 mM EGTA) and homogenized with 10 strokes of a Dounce homogenizer (pestle A). Adenylate cyclase activity was measured by the method of Salomon et al., (18) on samples of either homogenate or membrane pellets obtained by centrifugation of diluted homogenates at 47,000×g for 30 min. The enzyme assay mix contained 0.1–0.3 mM [$\alpha$-$^{32}$P]ATP, MgCl$_2$, and guanine nucleotides, as specified in the tables and figures, and 1 mM cAMP, 5 mM phosphocreatine, and 100 U/ml creatine phosphokinase. Purified bovine PTH-(1–84), generously provided by Drs. H. Keutmann and M. Rosenblatt, Massachusetts General Hospital, Boston, Mass., was dissolved and diluted in 1.5 ml/liter acetic acid containing 1 g/liter bovine serum albumin (Pentex fraction V, Miles Laboratories, Elkhart, Ind.). L-Isoproterenol bitarate (Sigma Chemical Co., St. Louis, Mo.) was prepared immediately before use and dissolved and diluted in assay buffer. Control tubes were assayed in the presence of diluent alone.

We claim:

1. A peptide which is desamino[Leu$^{11}$,D-Trp$^{12}$,Lys$^{13}$(N$^\epsilon$-CO(CH$_2$)$_2$-Phenyl)]hHCF(8–34)NH$_2$.

2. An invitro bioassay of HCF, wherein radiolabeled HCF together with an effective amount of the peptide of claim 1 reacts with a HCF receptor, present in animal cells or membranes, and following the reaction, the amount of radiolabeled HCF bound to the receptor is measured.

3. A pharmaceutical composition having HCF antagonist activity comprising a pharmaceutically acceptable carrier and, dispersed therein, a therapeutically effective but non-toxic amount of a peptide of claim 1.

* * * * *